US009701946B2

(12) United States Patent
Chen et al.

(10) Patent No.: US 9,701,946 B2
(45) Date of Patent: Jul. 11, 2017

(54) PURIFICATION METHOD FOR EMBRYO—DERIVED INFECTIOUS BRONCHITIS VIRUS (IBV)

(71) Applicants: Zhaoqing Dahuanong Biological Medicine Co., Ltd, Zhaoqing (CN); South China Agricultural University, Guangzhou (CN)

(72) Inventors: Ruiai Chen, Zhaoqing (CN); Jiahua Xu, Zhaoqing (CN); Xinqiu Wang, Zhaoqing (CN); Dongxia Zhang, Zhaoqing (CN); Beibei Sun, Zhaoqing (CN); Xiaoyu Xie, Zhaoqing (CN); Changbao Ren, Zhaoqing (CN)

(73) Assignees: Zhaoqing Dahuanong Biological Medicine Co., Ltd, Zhaoqing (CN); South China Agricultural University, Guangzhou (CN)

( * ) Notice: Subject to any disclaimer, the term of this patent is extended or adjusted under 35 U.S.C. 154(b) by 0 days.

(21) Appl. No.: 14/944,223

(22) Filed: Nov. 18, 2015

(65) Prior Publication Data

US 2016/0222357 A1    Aug. 4, 2016

(30) Foreign Application Priority Data

Jan. 30, 2015 (CN) .......................... 2015 1 0049732

(51) Int. Cl.
*C12N 7/00* (2006.01)
*C12N 7/02* (2006.01)

(52) U.S. Cl.
CPC ................. *C12N 7/00* (2013.01); *C12N 7/02* (2013.01); *C12N 2770/20051* (2013.01)

(58) Field of Classification Search
None
See application file for complete search history.

(56) References Cited

U.S. PATENT DOCUMENTS

2006/0257852 A1*  11/2006  Rappuoli ............. C07K 14/005
                                                              435/5
2016/0222357 A1*  8/2016  Chen ........................ C12N 7/00

OTHER PUBLICATIONS

Guy, J. S. "Isolation and propagation of coronaviruses in embryonated eggs." Methods in molecular biology (Clifton, NJ) 454 (2008): 109-117.*
Guo et al (Derwent abstract of CN 102600468; Jul. 25, 2012).*
Liu et al (CN 102628032A; Aug. 8, 2012; WIPO translation provided).*
Zhao et al. (Journal of Virology. Sep. 2008; 82 (17): 8647-8655).*

* cited by examiner

*Primary Examiner* — Shanon A Foley
(74) *Attorney, Agent, or Firm* — Wayne & King LLC

(57) ABSTRACT

The invention discloses an avian infectious bronchitis virus purification method. The method uses ordinary avian embryo which was affected by avian bronchitis virus. Using the combination of centrifugation, ultrafiltration, concentration, molecular sieve chromatography and ultrafiltration method can effectively remove miscellaneous protein in embryo-derived infectious bronchitis virus antigen, high virus recovery, and have no effect on the activity of avian infectious bronchitis virus. The avian infectious bronchitis virus purified by this method can be directly used in the preparation of avian infectious bronchitis virus vaccine.

8 Claims, 1 Drawing Sheet

Fractions

Embryo - derived
Infectious Bronchitis Virus

PURIFICATION METHOD FOR EMBRYO—DERIVED INFECTIOUS BRONCHITIS VIRUS (IBV)

CROSS-REFERENCE TO RELATED APPLICATIONS

This application is a continuation in part of, and claims priority to, Chinese Patent Application No. 201510049732.4 with a filing date of Jan. 30, 2015. The content of the aforementioned application, including any intervening amendments thereto, is incorporated herein by reference.

TECHNICAL FIELD

The present invention relates to a method of purification of a virus, in particular to a method for the purification of avian Infectious Bronchitis Virus (IBV).

BACKGROUND OF THE INVENTION

Avian infectious bronchitis is an acute contagious respiratory infectious disease cause by infectious bronchitis virus. The clinical signs of infections are breathing difficulties, coughing and mouth breathing etc. Infectious bronchitis virus is a coronavirus. Its particles are spherical, with a diameter around 80~120 nm, sometimes are polymorphic, with capsule and many pear-shape spikes. The spikes are radially arranged with about 20 nm long and nucleocapsid helical symmetry structure. Avian infectious bronchitis virus genome is a single thread-like chain of positive-strand and single-stranded RNA molecule, with the size of 27000~32000 nt. It is the largest known RNA virus genome.

Avian infectious bronchitis is a vaccine-preventable disease. Vaccines are usually made of the virus which uses avian embryo for immune incubation reproduction. Avian infectious bronchitis virus antigen which was obtained from avian embryo usually contains a large number of avian embryo protein and other impurities. The traditional purification methods include ultra high speed centrifugation, density gradient centrifugation, sucrose gradient centrifugation. CsCl gradient centrifugation, PEG precipitation and ammonium sulfate precipitation. For example, Liu et al. teach a high-speed centrifugal separation method to purify virus in Chinese Patent application CN102628032A. These purification methods have many problems, such as, 1. Small process capacity; 2. Complex operation; 3. Introduction of exogenous impurities, such as sucrose, PEG, ammonium sulfate etc; 4. Degeneration of the virus, such as ammonium sulphate precipitation.

SUMMARY OF THE INVENTION

In order to overcome these deficiencies present in the existing technology, the current invention provide a purification method with high recovery rate, no exogenous impurities, and no effect on virus activity of embryo-derived avian infectious bronchitis virus.

To solve the above problems, the technical solutions used in the invention are following:
An embryo-derived avian infectious bronchitis virus purification method, comprising the following steps:
1) Inoculating an ordinary fertilized chicken embryo with avian Infectious Bronchitis Virus;
2) Incubating said embryo at 37° C. for 48-96 hours, then freezing said embryo at 2° C. to 8° C. for 8-16 hours, then collecting the allantoic fluid from said avian embryo;
3) Centrifuging said allantoic fluid with 4000-6000 rpm for 10-50 min;
4) Ultrafiltrating the centrifugal liquid from step 3) with ultrafiltration membrane which pore size is 30-500 kda, then concentrating the filtrate to 20%~50% of the original volume;
5) Chromatographing said concentrated filtrate with a molecular sieve, the said molecular sieve was packed with a column height of 30-120 cm; and the loading volume of the said concentrated filtrate was 5% to 20% of the volume of the packing molecular sieve filler; PBS buffer was the chromatography elution; the first protein peak elution was collected as avian infectious bronchitis virus;
6) Ultrafiltration: the avian infectious bronchitis virus elusion, obtained from step 5), was filtered by ultrafiltration membrane which pore size is 30-500 kda and concentrated its volume to 20%-50% of original volume;
In step 1), preferably, the avian embryo is about 9-11 hatching days;
In step 2), preferably, remove avian embryos died within 24 h;
In step 3), preferably, the centrifugal speed is 4500-5500 rpm;
In step 3), preferably, the centrifugal time is 20-40 min;
In step 5), preferably, the packing filler of molecular sieve is Superdex™ 200;
In step 5), preferably, the sample loading volume is 10%-20% of column volume;
In step 5), preferably, the elution velocity is 2-3 mL/min.

The method of purification of avian infectious bronchitis virus which was obtained by the method above applies in the preparation of avian infectious bronchitis virus vaccine.

Compared to the existing technology, the invention has the advantages that:

Present invention provide an embryo-derived avian infectious bronchitis virus purification methods, using ordinary avian embryo to cultivate avian bronchitis virus via centrifugation, ultrafiltration, a combination of molecular sieve chromatography and ultrafiltration method, to remove 85% and above of avian infectious bronchitis virus antigens in the avian embryo. Virus recovery rate is no less than 70%. This method introduces no exogenous impurities and has no effect on the activity of avian infectious bronchitis.

For a more complete understanding of the present disclosure and its advantages, reference is now made to the following descriptions, taken in conjunction with the accompanying drawings.

BRIEF DESCRIPTION OF THE DRAWINGS

FIG. 1. is a graph of sample molecular sieve chromatography

DETAILED DESCRIPTION OF THE EMBODIMENTS

The present invention provides an embryo-derived avian infectious bronchitis virus purification method, comprising the following steps:
1) Inoculating an ordinary fertilized chicken embryo with avian Infectious Bronchitis Virus;
2) Incubating said embryo at 37° C. for 48-96 hours, then freezing said embryo at 2° C. to 8° C. for 8-16 hours, then collecting the allantoic fluid from said avian embryo;
3) Centrifuging said allantoic fluid with 4000-6000 rpm for 10-50 min;

4) Ultrafiltrating the centrifugal liquid from step 3) with ultrafiltration membrane which pore size is 30-500 kda, then concentrating the filtrate to 30% of the original volume;
5) Chromatographing said concentrated filtrate with a molecular sieve, the said molecular sieve was packed with a column height of 30-120 cm; and the loading volume of the said concentrated filtrate was 5% to 20% of the volume of the packing molecular sieve filler; PBS buffer was the chromatography elution; the first protein peak elution was collected as avian infectious bronchitis virus;
6) Ultrafiltrating the avian infectious bronchitis virus elusion, which obtained from step 5), by ultrafiltration membrane which pore size is 30-500 kda and concentrated its volume to 30% of original volume;

Present invention provide an embryo-derived avian infectious bronchitis virus purification methods, using ordinary avian embryo to cultivate avian bronchitis virus via centrifugation, ultrafiltration, a combination of molecular sieve chromatography and ultrafiltration method, to remove 85% and above of impurity hybrid protein from avian infectious bronchitis virus antigens in the avian embryo. Viral recovery rate of the method is no less than 70%. This method has no effect on the activity of avian infectious bronchitis.

The current method increased the yield of allantoic fluid in incubating step with freezing the avian embryos overnight treatment. The current invention uses a low speed centrifugation, effectively reducing the viral damage. The present invention is a chromatographic sample is then ultrafiltration operation, can effectively remove the molecular weight less than the hybrid protein membrane pore size, especially on the sample volume to make up for a long time, viruses and other contaminating proteins difficult to separate defects. Sample ultrafiltering for the second time after chromatography can effectively remove the impurity protein which molecular weight is less than filter membrane pore size, particularly when loading large volume filtrate sample, virus and other impurity protein is difficult to separate.

The following detailed embodiments of the present invention will be further described below.

Embodiment 1

The present invention provides an embryo-derived avian infectious bronchitis virus purification method, comprising the following steps:
1) inoculation: 10 day old of fertilized chicken egg were inoculated avian infectious bronchitis virus with 0.1 mL/egg;
2) incubation: Embryo incubated at 37° C. for 72 hours, excluded avian embryos died within 24 hours, frozen at 2° C. to 8° C. for 8 hours, then allantoic fluid in avian embryo was collected;
3) centrifugation: Allantoic fluid was centrifuged at 4500 rpm for 30 min;
4) ultrafiltration: the infectious bronchitis virus elusion, obtained from step 3), was filtered by ultrafiltration membrane which pore size is 100 kDa and concentrated its volume to 30% of the original volume;
5) Chromatography: Superdex™ 200 molecular sieve was packed to the height of 40 cm in the column; the sample after ultrafiltration was loaded 5% of the packing volume, with PBS buffer (pH=7.4) for elution chromatography with a flow rate 2 mL/min; the first protein peak elution was collected as infectious bronchitis virus;
6) ultrafiltration: the infectious bronchitis virus elusion, obtained from step 5), was filtered by ultrafiltration membrane which pore size is 100 kDa and concentrated its volume to 30% of the original volume;

In the present embodiment, the $EID_{50}$ (50% Egg Infective Dose) of avian infectious bronchitis virus in step 1) is $10^{7.5}$/mL;

Embodiment 2 the present invention provides an embryo-derived avian infectious bronchitis virus purification method, comprising the following steps:
1) inoculation: 9 day old of fertilized chicken egg were inoculated avian infectious bronchitis virus with 0.12 mL/egg:
2) incubation: Embryo incubated at 37° C. for 96 hours, removed avian embryos died within 24 hours, frozen at 2° C. to 8° C. for 16 hours, allantoic fluid in avian embryo was collected;
3) centrifugation: Allantoic fluid was centrifuged at 4000 rpm for 50 min;
4) ultrafiltration: the infectious bronchitis virus elusion, obtained from step 3), was filtered by ultrafiltration membrane which pore size is 30 kDa.
5) Chromatography: Superdex™ 200 molecular sieve was packed to the height of 120 cm in the column; the sample after ultrafiltration was loaded about 20% of the packing volume, with PBS buffer (pH=7.4) for elution chromatography with a flow rate 3 mL/min; then the first protein peak elution was collected as infectious bronchitis virus;
6) ultrafiltration: the infectious bronchitis virus elusion, obtained from step 5), was filtered by ultrafiltration membrane which pore size is 100 kDa In the present embodiment, the $EID_{50}$ of avian infectious bronchitis virus in step 1) is $10^{7.5}$/mL;

Embodiment 3

The present invention provides an embryo-derived avian infectious bronchitis virus purification method, comprising the following steps:
1) inoculation: 11 day old of fertilized chicken egg were inoculated avian infectious bronchitis virus with 0.8 mL/egg and the $EID_{50}$ of the avian infectious bronchitis virus is $10^{7.0}$/mL;
2) incubation: Embryo incubated at 37° C. for 48 hours, removed avian embryos died within 24 hours, frozen at 2° C. to 8° C. for 12 hours, then allantoic fluid in avian embryo was collected;
3) centrifugation: Allantoic fluid was centrifuged at 5500 rpm for 20 minutes;
4) ultrafiltration: the infectious bronchitis virus elusion, which obtained from step 3), was filtered by ultrafiltration membrane which pore size is 500 kDa;
5) Chromatography: Superdex™ 200 molecular sieve was packed to the height of 80 cm in the column; the sample after ultrafiltration was loaded 10% of the packing volume, with PBS buffer (pH=7.4) for elution chromatography with a flow rate 3 mL/min; the first protein peak elution was collected as infectious bronchitis virus;
6) ultrafiltration: the infectious bronchitis virus elusion, obtained from step 5), was filtered by ultrafiltration membrane which pore size is 500 kDa and concentrated.

In the present embodiment, the $EID_{50}$ of avian infectious bronchitis virus in step 1) is $10^{7.5}$/mL;

Present invention provide an embryo-derived avian infectious bronchitis virus purification methods, to remove 85% and above of avian infectious bronchitis virus antigens in the avian embryo. Virus recovery rate is no less than 70%. This method has no effect on the activity of avian infectious bronchitis virus. After this purification method, the virus can be used for further preparation of avian infectious bronchitis virus vaccine.

Purification Performance Testing

Testing protein content in each step by using UV spectrophotometer at 280 nm wavelength and inoculation of avian embryo to determine the avian infectious bronchitis virus survival rate or virus recovery rate.

The embodiment 3 protein content of molecular sieve chromatography is shown in FIG. 1.

The calculation formula of avian infectious bronchitis survival rate of recovery rate is shown below:

$$\text{Recovery rate} = \frac{EID_{50}(\text{actural}) \times V(\text{actural})}{EID_{50}(\text{initial}) \times V(\text{initial})} \times 100\%$$

The protein removal rate is calculated as flows:

$$\text{Protein removal rate} = \frac{C(\text{initial}) - C(\text{actural})}{C(\text{initial})} \times 100\%$$

Wherein C (initial): Initially the total protein content in the sample; C (actual): the total protein content in the actual testing; the protein content and virus recovery rate from different separation step is shown in Table 1; the protein content and virus recovery rate from Table 1;

TABLE 1

| Step | Name | $EID_{50}$ | Virus recovery rate | Protein removal rate |
|---|---|---|---|---|
| 3 | centrifugation | $10^{7.5}$/mL | 90% | 5% |
| 4 | ultrafiltration | $10^{7.4}$/mL | 89% | 45% |
| 5 | Molecular sieve | $10^{7.3}$/mL | 80% | 85% |
| 6 | ultrafiltration | $10^{7.2}$/mL | 76% | 90% |

From the result of Table 1, centrifugation in step 4) has less damage on the virus, and the virus recovery rate is up to 90%. With molecular sieve chromatography in step 5), the recovery rate of the virus is about 80%, and the protein removal rate can reach about 85%. With ultrafiltration in step 6), the protein removal rate can get up to 90%, and the virus recovery rate can still be 76%. So, this invention provides a method for purification and isolation of avian infectious bronchitis virus. And this virus can meet the requirement of vaccine. (The sample volumes of $EID_{50}$ test before and after purification process are same (By dilution).)

The method provided by this invention can also be used for qualitative detection of the virus;

Comparison of Embodiment 1

A series tests were performed with different centrifugal speed and time, and the separation results of avian infectious bronchitis virus in chicken embryos liquid are shown in table 2. (Virus lost percentage=1−virus recovery rate, want to focus the precipitation of virus loss)

TABLE 2 the effect of centrifugal speed and time on virus separation

| | | Centrifugal speed (rpm) | | | | | | |
|---|---|---|---|---|---|---|---|---|
| | | 4000 | 4500 | 5000 | 5500 | 6000 | 7000 | 8000 |
| 10 min | Virus loss | 1% | 2% | 2% | 3% | 3% | 8% | 15% |
| | precipitation | little | little | little | little | little | much | much |
| 20 min | Virus loss | 3% | 3% | 4% | 4% | 8% | 20% | 25% |
| | precipitation | more | more | more | more | much | much | much |
| 30 min | Virus loss | 4% | 4% | 4% | 5% | 10% | 35% | 50% |
| | precipitation | more | more | more | more | much | much | much |
| 40 min | Virus loss | 6% | 6% | 7% | 7% | 12% | 40% | 60% |
| | precipitation | more | more | more | more | much | much | much |
| 50 min | Virus loss | 9% | 9% | 11% | 12% | 16% | 55% | 70% |
| | precipitation | much | much | much | much | much | much | much |

Table 2 results show that with the increase of the centrifugal speed and extend the centrifugation time, the amount of damage the virus increases, more massive impurities can be separated. When the centrifugal speed is 4500 rpm-5500 rpm, centrifugal time is 20-40 minutes, the virus loss in the chicken embryo is no more than 10%, and more massive impurities can be removed.

Comparison of Embodiment 2

When collecting embryonic fluid, the influence of the temperature and storage time for each embryo liquid yield are shown in table 3:

TABLE 3 the influence of temperature and storage time for each embryo liquid yield.

| | storage time | | | | | |
|---|---|---|---|---|---|---|
| | 2 h | 4 h | 8 h | 12 h | 16 h | 24 h |
| | 25° C. | | | | | |
| Amount(mL/egg) | 3 | 3 | 4 | 3 | 3 | 4 |
| | 2 to 8° C. | | | | | |
| Amount(mL/egg) | 4 | 6 | 8 | 10 | 11 | 10 |

Table 3 results illustrate that the chicken embryo after incubation can get less chicken embryo fluid when kept at room temperature (25° C.), while keep at 2° C.-8° C. for 8-16 h, the chicken embryo amount allantoic fluid is 2-3 times more than the liquid stored at room temperature (25° C.). With keeping embryo more than 16 h, each of chicken embryo liquid yields was slightly less.

The implementation of the method is only for the preferred embodiment of the invention, and cannot be used for define the scope of protection of the invention, the technician in the field of any non-substantive change and replacement of the present invention are required to protect the scope of the present invention.

We claim:
1. A purification method for Embryo-derived avian Infectious Bronchitis Virus (IBV), comprising the following steps:
   1) Inoculating fertilized eggs containing chicken embryos with avian Infectious Bronchitis Virus;
   2) incubating the eggs containing the embryos at 37° C. for 48-96 hours, removing the eggs containing the avian embryos that have died within the first 24 hours during embryo incubation; refrigerating the remaining eggs containing the embryos at 2° C. to 8° C. for 8-16 hours for storage, then collecting the allantoic fluid from the eggs;

3) Centrifuging the allantoic fluid at 4000-6000 rpm for 10-50 min;

4) Ultrafiltrating the centrifugal liquid from step 3) with ultrafiltration membrane which pore size is 30-500 kDa, concentrating the filtrate to 20%-50% of the original volume;

5) Chromatographing the concentrated filtrate with a molecular sieve (with a column height of 30-120 cm packing); loading the concentrated filtrate with a loading volume (5% to 20% of the column volume, eluting the chromatography with PBS buffer solution, and collecting the first protein elution peak as avian infectious bronchitis virus;

6) Ultrafiltrating the avian infectious bronchitis virus elusion from step 5) with ultrafiltration membrane which pore size is 30-500 kDa and concentrating the filtrate to 20%-50% of the original volume.

2. A purification method according to claim 1, wherein step 1), the fertilized chicken embryo is at 9-11 days of embryonation.

3. A purification method according to claim 1, wherein step 3), further comprising the centrifugal speed is 4500-5500 rpm.

4. A purification method according to claim 1, wherein step 3), further comprising the centrifugal time is 20-40 minutes.

5. A purification method according to claim 1, wherein step 5), further comprising the packing filler of molecular sieve is Superdex™ 200.

6. A purification method according to claim 1, wherein step 5), further comprising the sample loading volume is 10%-20% of column volume.

7. A purification method according to claim 1, wherein step 5), further comprising the elution velocity is 2-3 mL/min.

8. A purification method according to claim 1, the method of purification of avian infectious bronchitis virus applies in the preparation of avian infectious bronchitis virus vaccine.

* * * * *